(12) United States Patent (10) Patent No.: US 9,320,427 B2
Levien et al. (45) Date of Patent: Apr. 26, 2016

(54) COMBINATION OPTICAL AND ULTRASONIC IMAGING OF AN EYE

(71) Applicants: Andrew K. Levien, Morrison, CO (US); John D. Watson, Evergreen, CO (US)

(72) Inventors: Andrew K. Levien, Morrison, CO (US); John D. Watson, Evergreen, CO (US)

(73) Assignee: ArcScan, Inc., Morrison, CO (US)

( * ) Notice: Subject to any disclaimer, the term of this patent is extended or adjusted under 35 U.S.C. 154(b) by 225 days.

(21) Appl. No.: 13/937,948

(22) Filed: Jul. 9, 2013

(65) Prior Publication Data

US 2014/0009741 A1 Jan. 9, 2014

Related U.S. Application Data

(60) Provisional application No. 61/669,400, filed on Jul. 9, 2012.

(51) Int. Cl.
*A61B 3/14* (2006.01)
*A61B 3/00* (2006.01)
(Continued)

(52) U.S. Cl.
CPC . *A61B 3/102* (2013.01); *A61B 3/14* (2013.01); *A61B 3/145* (2013.01); *A61B 8/10* (2013.01);
(Continued)

(58) Field of Classification Search
CPC .......... A61B 8/4461; A61B 8/13; A61B 8/42; A61B 5/0066; A61B 5/0073; A61B 5/0095; A61B 3/102; A61B 3/0083; A61B 3/10; A61B 3/14; A61B 3/145; A61B 1/00172; A61B 6/5247; A61B 8/4416; A61B 8/4209; A61B 8/4281; A61B 8/4245; G01B 9/0205; G01B 9/02091; G01S 15/8913

USPC ......... 600/425, 427, 437, 445, 452, 459, 472; 351/206, 246, 245; 702/104; 73/1.82
See application file for complete search history.

(56) References Cited

U.S. PATENT DOCUMENTS 3,371,660 A 3/1968 Benson
3,821,891 A 7/1974 Collins et al.
(Continued)

FOREIGN PATENT DOCUMENTS

CA 2295431 7/2001
CA 2299483 7/2001
(Continued)

OTHER PUBLICATIONS

Angelson et al. "Which transducer array is best?" European Journal of Ultrasound, 1995, vol. 2., pp. 151-164.
(Continued)

*Primary Examiner* — Bumsuk Won
*Assistant Examiner* — Collin X Beatty
(74) *Attorney, Agent, or Firm* — Sheridan Ross P.C.

(57) ABSTRACT

A method and apparatus are disclosed for integrating optical coherence tomography (OCT) and very high frequency ultrasound (VHFU) imaging systems. An OCT probe and reference arm are mounted along with an ultrasound probe on a carriage capable of rotational, linear, and/or arcuate motion. The probe carriage may be immersed in water or other suitable medium. The OCT and VHFU probes move about the cornea surface such that the probe axes are substantially perpendicular relative to the cornea surface throughout a scan. The probes are able to be scanned in an arcuate path across the entire cornea surface. The method and apparatus disclosed are also directed towards providing a positioning mechanism and scan head comprising an arcuate guide track wherein only an OCT probe is mounted on the probe carriage. This embodiment allows the OCT probe beam to remain substantially perpendicular to the cornea and lens surfaces.

4 Claims, 9 Drawing Sheets

(51) Int. Cl.
*A61B 3/10* (2006.01)
*A61B 8/10* (2006.01)
*A61B 8/00* (2006.01)

(52) U.S. Cl.
CPC ............... *A61B 8/42* (2013.01); *A61B 8/4209* (2013.01); *A61B 8/4281* (2013.01); *A61B 8/4416* (2013.01); *A61B 8/4461* (2013.01); *A61B 8/4245* (2013.01)

(56) References Cited

U.S. PATENT DOCUMENTS

| | | |
|---|---|---|
| 3,997,793 A | 12/1976 | Rogers et al. |
| 4,114,214 A | 9/1978 | VonHeck |
| 4,154,114 A | 5/1979 | Katz |
| 4,183,249 A | 1/1980 | Anderson |
| 4,206,763 A | 6/1980 | Pedersen |
| 4,227,780 A | 10/1980 | Ohta et al. |
| 4,245,250 A | 1/1981 | Tiemann |
| 4,347,213 A | 8/1982 | Rogers |
| 4,484,569 A | 11/1984 | Driller et al. |
| 4,493,877 A | 1/1985 | Burnett |
| 4,550,607 A | 11/1985 | Maslak et al. |
| 4,564,018 A | 1/1986 | Hutchison et al. |
| 4,807,634 A | 2/1989 | Enjoji et al. |
| 4,815,047 A | 3/1989 | Hart |
| 4,817,432 A | 4/1989 | Wallace et al. |
| 4,823,801 A | 4/1989 | Sakane |
| 4,858,124 A | 8/1989 | Lizzi et al. |
| 4,858,613 A | 8/1989 | Fry et al. |
| 4,930,512 A | 6/1990 | Henriksen et al. |
| 4,932,414 A | 6/1990 | Coleman et al. |
| 5,029,587 A | 7/1991 | Baba et al. |
| 5,079,786 A | 1/1992 | Rojas |
| 5,103,517 A | 4/1992 | Krouskop |
| 5,116,114 A | 5/1992 | Nakamura et al. |
| 5,293,871 A | 3/1994 | Reinstein et al. |
| 5,331,962 A | 7/1994 | Coleman et al. |
| 5,369,454 A | 11/1994 | Reinstein et al. |
| 5,387,180 A | 2/1995 | Lehmer |
| 5,460,179 A | 10/1995 | Okunuki et al. |
| 5,474,070 A | 12/1995 | Ophir et al. |
| 5,487,388 A | 1/1996 | Rello et al. |
| 5,551,432 A | 9/1996 | Iezzi |
| 5,556,169 A | 9/1996 | Parrish et al. |
| 5,614,099 A | 3/1997 | Hirose et al. |
| 5,626,150 A | 5/1997 | Johnson et al. |
| 5,626,594 A | 5/1997 | Smith |
| 5,776,068 A | 7/1998 | Silverman et al. |
| 5,826,583 A | 10/1998 | Wood |
| 5,832,550 A | 11/1998 | Hauger et al. |
| 5,855,207 A | 1/1999 | Moenning et al. |
| 5,906,205 A | 5/1999 | Hiebert |
| 5,966,763 A | 10/1999 | Thomas et al. |
| 5,971,006 A | 10/1999 | Seigerschmidt |
| 6,053,613 A | 4/2000 | Wei et al. |
| 6,145,143 A | 11/2000 | Hicks et al. |
| 6,154,204 A | 11/2000 | Thompson et al. |
| 6,198,956 B1 | 3/2001 | Dunne |
| 6,315,727 B1 | 11/2001 | Coleman et al. |
| 6,318,372 B1 | 11/2001 | Hiebert |
| 6,334,227 B1 | 1/2002 | Larger |
| 6,374,439 B2 | 4/2002 | Heimbrock et al. |
| 6,460,207 B1 | 10/2002 | Papay et al. |
| 6,487,447 B1 | 11/2002 | Weimann et al. |
| 6,491,637 B2 | 12/2002 | Foster et al. |
| 6,574,813 B2 | 6/2003 | Bolden et al. |
| 6,629,929 B1 | 10/2003 | Jago et al. |
| 6,684,433 B2 | 2/2004 | Giori et al. |
| 6,837,855 B1 | 1/2005 | Puech |
| 6,868,569 B2 | 3/2005 | VanSteenburg |
| 6,887,203 B2 | 5/2005 | Phillips et al. |
| 6,923,767 B2 | 8/2005 | Saied et al. |
| 6,981,417 B1 | 1/2006 | Oravecz |
| 7,048,690 B2 | 5/2006 | Coleman et al. |
| 7,168,116 B2 | 1/2007 | Reger et al. |
| 7,237,898 B1* | 7/2007 | Hohla et al. ............... 351/246 |
| 7,356,905 B2 | 4/2008 | Ketterling et al. |
| 7,451,507 B2 | 11/2008 | Brinkerhoff et al. |
| 7,454,024 B2 | 11/2008 | Ketterling et al. |
| 7,474,041 B2 | 1/2009 | Ketterling et al. |
| 7,480,058 B2 | 1/2009 | Zhao et al. |
| 7,708,342 B2 | 5/2010 | Leach |
| 8,064,989 B2 | 11/2011 | Brown et al. |
| 8,115,935 B2 | 2/2012 | Everett et al. |
| 8,317,709 B2 | 11/2012 | Eilers et al. |
| 8,496,588 B2 | 7/2013 | Eilers et al. |
| 8,510,883 B2 | 8/2013 | Eilers et al. |
| 2002/0085173 A1 | 7/2002 | Schippert et al. |
| 2002/0143252 A1 | 10/2002 | Dunne et al. |
| 2003/0004416 A1 | 1/2003 | Phillips et al. |
| 2003/0142269 A1 | 7/2003 | Cumming |
| 2004/0220478 A1 | 11/2004 | Wallace et al. |
| 2005/0120479 A1 | 6/2005 | Habashi et al. |
| 2006/0029525 A1 | 2/2006 | Laugharn, Jr. et al. |
| 2006/0241533 A1 | 10/2006 | Geller |
| 2006/0288487 A1 | 12/2006 | Roleder et al. |
| 2007/0083995 A1 | 4/2007 | Purdy et al. |
| 2007/0239030 A1 | 10/2007 | Prager et al. |
| 2007/0276233 A1 | 11/2007 | Besson et al. |
| 2008/0097214 A1 | 4/2008 | Meyers et al. |
| 2009/0192389 A1* | 7/2009 | Eilers et al. ............... 600/459 |
| 2009/0234369 A1 | 9/2009 | Bax et al. |
| 2010/0004538 A1 | 1/2010 | Eilers et al. |
| 2010/0031448 A1 | 2/2010 | Hijlkema |
| 2010/0217125 A1 | 8/2010 | Kadokura et al. |
| 2010/0229306 A1 | 9/2010 | Reeder et al. |
| 2010/0249562 A1* | 9/2010 | Zhang et al. ............... 600/365 |
| 2012/0320368 A1* | 12/2012 | Jiao et al. ............... 356/72 |
| 2013/0072755 A1 | 3/2013 | Papania et al. |
| 2013/0085370 A1* | 4/2013 | Friedman et al. ............ 600/400 |
| 2013/0144171 A1 | 6/2013 | Watson |
| 2014/0249422 A1 | 9/2014 | Eilers et al. |

FOREIGN PATENT DOCUMENTS

| | | |
|---|---|---|
| CA | 2395203 | 7/2001 |
| CA | 2409234 | 4/2004 |
| JP | 2006-149001 | 6/2006 |

OTHER PUBLICATIONS

U.S. Appl. No. 13/796,931, filed Mar. 12, 2013, Levien.
U.S. Appl. No. 13/894,741, filed May 15, 2013, Watson et al.
Binder, "SL-OCT and Ultrasound Support the Need for New Phakic IOL Sizing Strategies," Euro Times, Mar. 2007, p. 11.
Coleman et al., "Ultrasonography of the Eye and Orbit," Second Edition, published by Lippincott Williams & Wilkins, 2006, pp. 1-186.
Izatt et al., "Theory of Optical Coherence Tomography," Chap. 2 of "Optical Coherence Tomography Technology and Applications," Drexler and Fujimoto eds, ISBN:978-3-540-77549-2, 2008, pp. 47-72.
Ketterling, "Design and Fabrication of a 40-MHz Annular Array Transducer," IEEE Transactions on Ultrasonics, Ferroelectrics, and Frequency Control, Apr. 2005, vol. 52, No. 4, pp. 672-681.
Ketterling, "Operational Verification of a 40-MHz Annular Array Transducer," IEEE Transactions on Ultrasonics, Ferroelectrics, and Frequency Control, Mar. 2006, vol. 53, No. 3, pp. 623-630.
Mamou, "Chirp-Coded Excitation Imaging With a High-Frequency Ultrasound Annular Array," IEEE Transactions on Ultrasonics, Ferroelectrics, and Frequency Control, Feb. 2008, vol. 55, No. 2, pp. 508-513.
Pinero et al., "Equivalence, Differences Identified in Biometric Analysis," Cataract & Refractive Surgery Today, Mar. 2008, vol. 3, No. 12, pp. 46-49.
Reinstein et al., "Repeatability of Layered Corneal Pachymetry with the Artemis Very High Frequency Digital Ultrasound Arc-Scanner," J. Refractive Surg., vol. 26(9), 2009, original article, 6 pages.
Reinstein, "Subsurface Screening for Keratoconus—Accurate Measurements of the Epithelial and Stromal Layers Aid in Diagnosis," Cataract and Refractive Surgery Today, May 2007, pp. 88-89.

(56) References Cited

OTHER PUBLICATIONS

Roholt, "Sizing the Visian ICL," Cataract and Refractive Surgery Today, May 2007, p. 50.

Silverman at al., "Improved System for Sonographic Imaging and Biometry of the Cornea," J. Ultrasound Med., 1997, vol. 16, pp. 117-124.

* cited by examiner

COMBINATION OPTICAL AND ULTRASONIC IMAGING OF AN EYE

CROSS-REFERENCE TO RELATED APPLICATIONS

This application claims the benefits, under 35 U.S.C. §119 (e), of U.S. Provisional Application Ser. No. 61/669,400 entitled "Combination Optical and Ultrasonic Imaging of an Eye" filed Jul. 9, 2012 which is incorporated herein by reference.

FIELD

The present disclosure relates in general to optical and ultrasonic imaging of biological materials, such as the cornea and natural lens of the eye and, in particular, relates to a device and methods of combining Optical Coherence Tomography ("OCT") and Very High Frequency Ultrasound ("VHFU") imaging technologies into a single ophthalmic imaging system.

BACKGROUND

The many benefits and methods of mounting a Very High Frequency Ultrasound ("VHFU") probe on an arcuate guide track have been discussed in prior patents and published patent applications. Ultrasound imaging systems are described in each of the following patent applications, all of which are incorporated by reference:

1. U.S. Pat. No. 8,317,709 entitled "Alignment and Imaging of an Eye with an Ultrasonic Scanner" issued Nov. 27, 2012.
2. U.S. patent application Ser. No. 12/347,674, entitled "Innovative Components for an Ultrasonic Arc Scanning Apparatus" filed Dec. 31, 2008.
3. U.S. patent application Ser. No. 12/754,444 entitled "Method of Positioning a Patient for Medical Procedures" filed Apr. 5, 2010.
4. U.S. patent application Ser. No. 12/418,392 entitled "Procedures for an Ultrasonic Arc Scanning Apparatus" filed Apr. 3, 2009.

Ultrasonic imaging has been used in corneal procedures such as LASIK to make accurate and precise images and maps of cornea thickness which includes epithelial thickness, Bowman's layer and images of LASIK flaps. These images have an A-scan resolution of about 35 microns and have been shown to attain repeatability of better than about 1 micron. This repeatability is discussed in "Repeatability of Layered Corneal Pachymetry with the Artemis Very High Frequency Digital Ultrasound Arc-Scanner" by D. Z. Reinstein, T. J. Archer, M. Gobbe, R. H. Silverman and D. J. Coleman, MD in the Journal of Refractive Surgery November 2009.

A key contribution to the accurate and precise cornea layer measurement achieved by ultrasonic imaging systems is attributed to the arcuate movement of the ultrasound probe around the cornea surface such that the probe remains substantially perpendicular to the cornea surface at all times during the scan. Maintaining the ultrasound probe aligned substantially perpendicular to the cornea surface during the scan assures maximum possible reflectance of the ultrasound beam from the cornea and provides superior signal to noise ratios of echoes of not only the anterior and posterior surfaces of the cornea, but all intermediate biologic interfaces, most notably of Bowman's interface which separates the epithelium from the stroma.

Given the high diagnostic value of the epithelium thickness map this ultrasound imaging technology provides, other imaging technologies are now being adapted to provide similar capabilities of epithelium thickness mapping. A promising example is Optical Coherence Tomography ("OCT") systems which use infrared light. OCT systems have the potential to produce higher image resolution based on the relatively small wavelength of the infrared light they use compared to the long wavelength used by VHFU platforms. OCT systems have been developed for both general anterior segment imaging and retinal scanning OCT systems have been demonstrated to be a very effective high precision imaging technology, particularly for ocular structures (such as the cornea and the natural lens) that are transparent to the infrared light they use. However, the ability of OCT systems to image into opaque tissues is limited to a depth of about 1 to about 2 mm.

There are several challenges presented in the use of OCT platforms to image an eye. The practically achievable image resolution and precision of an OCT platform is very much a function of the strength of the reflected signal relative to noise. The strength of the reflected signal is driven largely, but not entirely, by the electric field reflectivity profile along the axis of the infrared beam. For generally opaque tissues which present strong reflectors at a number of angles the reflectivity profile is quite strong over a wider range of angles of the incident infrared beam relative to the tissue surface. However, the transparent structures of the eye pose a unique challenge as they are specular and as such provide a very high reflectance for a beam perpendicular to the surface but the rate of reflectance falls off rapidly as the beam strikes the surface at an oblique angle.

Most current OCT systems scan the imaging beam across the image field with the beam at a fixed angle and aligned with the visual axis of the eye. In these OCT systems, as the image beam is scanned further away from the visual axis, the image beam angle relative to the specular surfaces of the cornea layers (as an example) becomes more oblique and reflectance begins to drop quickly. To overcome this problem, some OCT systems employ over-sampling, surface curve fit, eye movement tracking (because of longer sample times from over-sampling) and many other signal and image processing techniques. Although these techniques may generally provide adequate results, these techniques increase the complexity and cost of OCT systems and in some cases increase the amount of time necessary to complete a scan.

The resolution and precision of OCT systems used to image cornea layers is further aggravated by the fact that the impedance differences between the cornea layers is quite small because the cornea is designed to transmit as much light as possible. These challenges, beam alignment to specular surfaces and low impedance difference within the cornea layers, serially combined are very difficult to overcome for commercially useful imaging of the cornea layers with OCT systems.

The fixed angle scanning of most OCT imaging systems develops yet another challenge unique to imaging specular surfaces. All current diagnostic OCT systems are non-contact systems, meaning the OCT beam travels through air before entering the specular surface of the cornea. Because the impedance mismatch between air and the cornea is quite large, as anyone skilled in the art will appreciate, a significant refraction correction must be made particularly as the angle between the incident beam and the cornea surface becomes more oblique. Therefore the thickness measurements of the cornea away from the central axis must also be corrected for refraction errors and poses another source of measurement error.

There remains, therefore, a need for improved systems and methods of OCT imaging that can be used to map the thickness of cornea layers with precision by overcoming the challenges of poor electric field reflectivity profiles, low reflected light amplitude due to lack of beam alignment to specular surfaces of the eye, and refraction corrections that are particularly acute away from the visual axis.

SUMMARY

These and other needs are addressed by the present disclosure. The various embodiments and configurations of the present disclosure are directed generally to methods of integrating OCT imaging technology (spectral domain and swept source) into a VHFU imaging system such as disclosed in the above referenced patents and patent applications. It is also disclosed to use a positioning mechanism and scan head comprising an arcuate guide track wherein only an OCT probe is mounted on the probe carriage. This embodiment allows the OCT probe beam to remain substantially perpendicular to the cornea and lens surfaces.

In one embodiment, a scanning device is disclosed comprising an instrument body configured to position an eye of a patient, the instrument body comprising a chamber; a positioning assembly connected to the instrument body; a scan head connected to the positioning assembly, the scan head comprising at least one guide track and at least one probe carriage; at least one optical probe attached to the probe carriage; wherein the at least one probe carriage moves along at least one guide track; wherein one of the at least one guide tracks is an arcuate guide track; and wherein the at least one probe emits and receives a pulse reflected from one or more components of the patient's eye. Further, the scanning device may include an optical imaging probe which is an optical coherence tomography probe and an ultrasound imaging probe.

In another embodiment, a method and imaging device are provided comprising: (a) positioning a patient to engage a scanning system, the scanning system comprising: an instrument body configured to engage the patient and position the patient's head and an eye; a positioning assembly connected to the instrument body, the positioning assembly comprising a scan head, the scan head comprising at least one guide track, at least one probe carriage, at least one optical imaging probe; wherein the scan head assembly is connected to the positioning assembly, wherein one of the at least one guide tracks is an arcuate guide track and wherein the at least one probe carriage moves along the at least one guide track; (b) moving, by a microprocessor, the at least one optical imaging probe along the at least one guide track while emitting and receiving optical pulses reflected from one or more components of the patient's eye; (c) recording, by the microprocessor, the received optical pulses on a tangible and non-transitory computer readable medium; and (d) providing, by the microprocessor, an optical image of a patient's eye. In this embodiment, the probe carriage may include at least one optical imaging probe which is an optical coherence tomography probe and at least one ultrasound imaging probe, the method further comprising; (a) moving, by the microprocessor, at least one ultrasound imaging probe and the at least one optical imaging probe along the at least one guide track while emitting and receiving ultrasound pulses reflected from one or more components of the patient's eye and, while at substantially the same time, the at least one optical imaging probe emits and receives an optical pulse reflected from one or more components of the patient's eye; (b) recording, by the microprocessor, the received ultrasound pulses and received optical pulses on a tangible and non-transitory computer readable medium; and (c) providing, by the microprocessor, an ultrasound image and an optical image of a patient's eye.

In yet another embodiment, an imaging device is provided, comprising an instrument body configured to position an eye of a patient, the instrument body comprising a chamber; a linear carriage operable to move along a linear guide track to displace linearly an arcuate guide track; at least one probe carrier comprising at least one of an ultrasound imaging probe and an optical imaging probe, operable to move along an arcuate guide track to displace arcuately the at least one ultrasound imaging probe and at least one optical imaging probe wherein; the linear carriage is attached to a positioning assembly, the linear carriage supports the arcuate guide track; and the arcuate guide track supports the probe carrier; the ultrasound imaging probe is operable to generate an ultrasound scan image of an ocular feature, and the optical imaging probe is operable to generate an optical image of the ocular feature.

The above-described embodiments and configurations are neither complete nor exhaustive. As will be appreciated, other embodiments of the disclosure are possible utilizing, alone or in combination, one or more of the features set forth above or described in detail below.

The following definitions are used herein:

The phrases at least one, one or more, and and/or are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

An acoustically reflective surface or interface is a surface or interface that has sufficient acoustic impedance difference across the interface to cause a measurable reflected acoustic signal. A specular surface is typically a very strong acoustically reflective surface.

Anterior means situated at the front part of a structure; anterior is the opposite of posterior.

An A-scan is a representation of a rectified, filtered reflected acoustic signal as a function of time, received by an ultrasonic transducer from acoustic pulses originally emitted by the ultrasonic transducer from a known fixed position relative to an eye component.

An accommodative lens, also known as a presbyopic lens or presby lens, is an intraocular lens implant that changes its focal distance in response to contraction of the ciliary muscle. When successfully implanted, an accommodative lens reverses presbyopia, the inability of the eye to change its focal distance from far to near.

Accuracy as used herein means free from error.

Aligning means positioning the transducer and transducer carriage track accurately and reproducibly in space with respect to a feature of the eye component of interest (such as the center of curvature or boundary of the cornea, lens, retina, etcetera).

The anterior chamber as used herein comprises the region of the eye from the front of the eye to the iris.

The anterior segment as used herein comprises the region of the eye from the front of the eye to just beyond the back of the lens.

An aperture refers to the ultrasonic transducer face which may be planar but is commonly shaped as a concave surface so as to form a focal point at a desired location in front of the transducer face.

An arc scanner is an ultrasound scanning device utilizing a transducer that both sends and receives pulses as it moves along an arcuate guide track, which guide track has a center of curvature whose position can be moved to scan different curved surfaces.

Arc scanning transducer center of curvature is the same as the center of curvature of the arc scanning guide.

Auto-centering means automatically, typically under computer control, causing centration of the arc scanning transducer with the eye component of interest.

The term automatic and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

A B-scan is a processed representation of A-scan data by either or both of converting it from a time to a distance using acoustic velocities and by using grayscales, which correspond to A-scan amplitudes, to highlight the features along the A-scan time history trace (the latter also referred to as an A-scan vector).

Center of rotation of the eye, there is a point within the eyeball that is more or less fixed relative to the orbit when the eye rotates in its orbit. It is considered that the center of rotation of an emmetropic eye (that is, a normal eye with about 20/20 vision) lies on the line of sight of the eye about 13.5 mm behind the anterior pole of the cornea when the line of sight of the eye is perpendicular to both the base line and the frontal plane.

Centration means aligning the center of curvature of the arc scanning transducer in space with the center of curvature of the eye component of interest (such as the cornea, lens, retina, etcetera) such that rays from the transducer pass through both centers of curvature. A special case is when both centers of curvature are coincident.

The ciliary body is the circumferential tissue inside the eye composed of the ciliary muscle and ciliary processes. There are three sets of ciliary muscles in the eye, the longitudinal, radial, and circular muscles. They are near the front of the eye, above and below the lens. They are attached to the lens by connective tissue called the zonule of Zinn, and are responsible for shaping the lens to focus light on the retina. When the ciliary muscle relaxes, it flattens the lens, generally improving the focus for farther objects. When it contracts, the lens becomes more convex, generally improving the focus for closer objects.

The term computer-readable medium as used herein refers to any storage and/or transmission medium that participate in providing instructions to a processor for execution. Such a medium is commonly tangible and non-transient and can take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

The terms determine, calculate and compute, and variations thereof, as used herein, are used interchangeably and include any type of methodology, process, mathematical operation or technique.

Fixation means having the patient focus an eye on an optical target such that the eye's optical axis is in a known spatial relationship with the optical target. In fixation, the light source is axially aligned in the arc plane with the light source in the center of the arc so as to obtain maximum signal strength such that moving away from the center of the arc in either direction results in signal strength diminishing equally in either direction away from the center.

The fovea is a small depression in the macula lutea of the retina where visual acuity is highest.

A guide is an apparatus for directing the motion of another apparatus.

Haptics are little curved hair-like protrusions extending from the outer diameter of some types of artificial lenses. Haptics attach these artificial lenses to the ciliary muscle by protruding into the sulcus and allow the artificial lens to accommodate in response to the action of the ciliary muscle in the same way the zonules cause the natural lens to accommodate in response to the action of the ciliary muscle.

The home position of the imaging ultrasound transducer is its position during the registration process.

An imaging ultrasound transducer is the device that is responsible for creating the outgoing ultrasound pulse and detecting the reflected ultrasound signal that is used for creating the A-Scans and B-Scans.

An intraocular lens is an artificial lens that is implanted in the eye to take the place of the natural lens.

LASIK is a procedure performed on the cornea for correcting naturally occurring refractive errors, such as myopia, hyperopia, and astigmatism. Commonly, an eximer laser selectively removes tissue from the inside of the cornea, after exposing it by cutting a thin flap, so as to reshape the external shape of the cornea.

The term means as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

As used herein, a meridian is a 2-dimensional plane section through the approximate center of a 3-dimensional eye and its angle is commonly expressed relative to a horizon defined by the nasal canthus and temporal canthus of the eye.

The term module as used herein refers to any known or later developed hardware, software, firmware, artificial intelligence, fuzzy logic, or combination of hardware and software that is capable of performing the functionality associated with that element.

The natural lens (also known as the aquula or crystalline lens) is a transparent, biconvex structure in the eye that, along with the cornea, helps to refract light to be focused on the retina. The lens, by changing shape, functions to change the focal distance of the eye so that it can focus on objects at various distances, thus allowing a sharp real image of the object of interest to be formed on the retina. This adjustment of the lens is known as accommodation. The lens is located in the anterior segment of the eye behind the iris. The lens is suspended in place by the zonular fibers, which attach to the lens near its equatorial line and connect the lens to the ciliary body. The lens has an ellipsoid, biconvex shape whose size and shape can change due to accommodation and due to growth during aging. The lens is comprised of three main parts: the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are found only on the anterior side of the lens.

Ocular as used herein means having to do with the eye or eyeball.

Ophthalmology as used herein means the branch of medicine that deals with the eye.

Optical as used herein refers to processes that use light rays.

The optical axis of the eye is the line of best fit joining the centers of curvature of the refracting surfaces (the anterior and posterior surfaces of the cornea and lens).

Optical Coherence Tomography (OCT) is a light based imaging technology that bases itself upon low coherence interferometry. In conventional interferometry with long coherence length (laser interferometry), interference of light occurs over a distance of meters. In OCT, this interference is shortened to a distance of micrometers, due to the use of broadband light sources (sources that can emit light over a broad range of frequencies). Light with broad bandwidths can be generated by using superluminescent diodes (superbright LEDs) or lasers with extremely short pulses (femtosecond lasers). An optical beam is directed at the tissue, and a small portion of this light that reflects from sub-surface features is collected and combined with reflection from a reference beam in a Michelson interferometer. Time domain based OCT systems require a moveable mirror in the reference beam to provide depth for the scanning field. Spectral domain and swept source OCT systems do not require a moveable mirror in the reference beam and instead us a spectrometer (usually diffraction grating) to separate frequency components in the interference signal which are in turn converted to reflectance profile along the beam axis. Application of OCT in this disclosure will emphasize the use of the spectral domain and swept source variants, as the elimination of the moveable mirror of the time domain technique represents an advantageous elimination of considerable mechanical detail in the reference arm.

Pachymetery or corneal pachymetery is technically referred to as Time Domain Reflectometry ultrasound. A pulse of ultrasonic energy is sent toward the cornea and the time spacing of the returning echoes are used to arrive at corneal thickness.

Phakic intraocular lenses, or phakic lenses, are lenses made of plastic or silicone that are implanted into the eye permanently to reduce a person's need for glasses or contact lenses. Phakic refers to the fact that the lens is implanted into the eye without removing the eye's natural lens. During phakic lens implantation surgery, a small incision is made in the front of the eye. The phakic lens is inserted through the incision and placed just in front of or just behind the iris.

A positioner means the mechanism that positions a scan head relative to a selected part of an eye. In the present disclosure, the positioning mechanism can move back and forth along the x, y or z axes and rotate in the $\beta$ direction about the z-axis. Normally the positioner does not move during a scan, only the scan head moves. In certain operations, such as measuring the thickness of a region, the positioner may move during a scan. The positioner may also be referred to as a positioning mechanism, a positioning assembly, and/or a positioning arm.

The posterior chamber as used herein comprises the region of the eye from the back of the iris to the front of the lens.

The posterior segment as used herein comprises the region of the eye from the back of the lens to the rear of the eye comprising the retina and optical nerve.

Precise as used herein means sharply defined.

Precision means how close in value successive measurements fall when attempting to repeat the same measurement between two detectable features in the image field. In a normal distribution, precision is characterized by the standard deviation of the set of repeated measurements. Precision is very similar to the definition of repeatability.

Presbyopia is caused by a loss of elasticity of the natural lens inside the eye. This occurs as part of the ageing process and, although it cannot be 'cured', it can be corrected by wearing glasses or implanting an artificial lens.

A probe as used herein means a measuring or testing device that converts variations in a physical quantity such as pressure or light into an electrical signal and vice versa. An ultrasound transducer holder comprising a transducer element and an OCT probe are examples of probes.

Refractive as used herein means anything pertaining to the focusing of light rays by the various components of the eye.

Registration means aligning.

Sector scanner is an ultrasonic scanner that sweeps out a sector like a radar. The swept area is pie-shaped with its central point typically located near the face of the ultrasound transducer.

Scan head means the mechanism that comprises at least one ultrasound transducer, at least one transducer holder, optionally an OCT sampling probe and an OCT reference arm and a transducer/probe carriage as well as any guide tracks that allow the transducer and probe to be moved relative to the positioner. Guide tracks may be linear, arcuate or any other appropriate geometry. The guide tracks may be rigid or flexible. Normally, only the scan head is moved during a scan.

Sector scanner is an ultrasonic scanner that sweeps a sector like a radar. The swept area is pie-shaped with its central point typically located near the face of the ultrasound transducer.

A specular surface as used herein means a mirror-like surface that strongly reflects either optical or acoustic waves. For example, an ultrasound beam emanating from a transducer will only be reflected directly back to that transducer when the beam is aligned substantially perpendicular to a specular surface.

The ciliary sulcus as used herein is the groove between the iris and ciliary body. The scleral sulcus is a slight groove at the junction of the sclera and cornea.

A track or guide track is an apparatus along which another apparatus moves.

Ultrasonic or ultrasound means sound that is above the ear's upper frequency limit. When used for imaging object like the eye, the sound passes through a liquid medium, and its frequency is many orders of magnitude greater than can be detected by the ear. For high-resolution acoustic imaging in the eye, the frequency is typically in the approximate range of about 5 to about 80 MHz.

Ultrasound probe means an assembly comprised of a transducer element (e.g., a piezoelectric material), a probe body and electrical conduits that carry transmitted and received signals from the transducer element to an A/D converter external to the probe.

Ultrasound pulse means a group of ultrasound waves centered around a center frequency where the pulse is comprised of at least one wave cycle. For example, the ultrasound pulse is a short burst of one to about ten wavelengths truncated at both ends of the wave train. An ultrasound pulse is further described in "Ultrasonography of the Eye and Orbit", Second Edition, Coleman et al., published by Lippincott Williams & Wilkins, 2006 which is incorporated herein by reference.

A vector refers to a single acoustic pulse and its multiple reflections from various eye components. An A-scan is a representation of this data whose amplitude is typically rectified.

VHUF means Very High Frequency Ultrasound where the frequency is typically in the approximate range of about 5 to about 80 MHz.

The visual axis of the eye is the line joining the object of interest and the fovea and which passes through the nodal points.

Zonules are tension-able ligaments extending from near the outer diameter of the crystalline lens and attach the natural lens to the ciliary body which allows the natural lens to accommodate in response to the action of the ciliary muscle.

BRIEF DESCRIPTION OF THE DRAWINGS

The present disclosure may take form in various components and arrangements of components, and in various steps and arrangements of steps. The drawings are only for purposes of illustrating some embodiments and are not to be construed as limiting the disclosure. In the drawings, like reference numerals refer to like or analogous components throughout the several views.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Ultrasound Eye Scanning Apparatus

Figure 1:
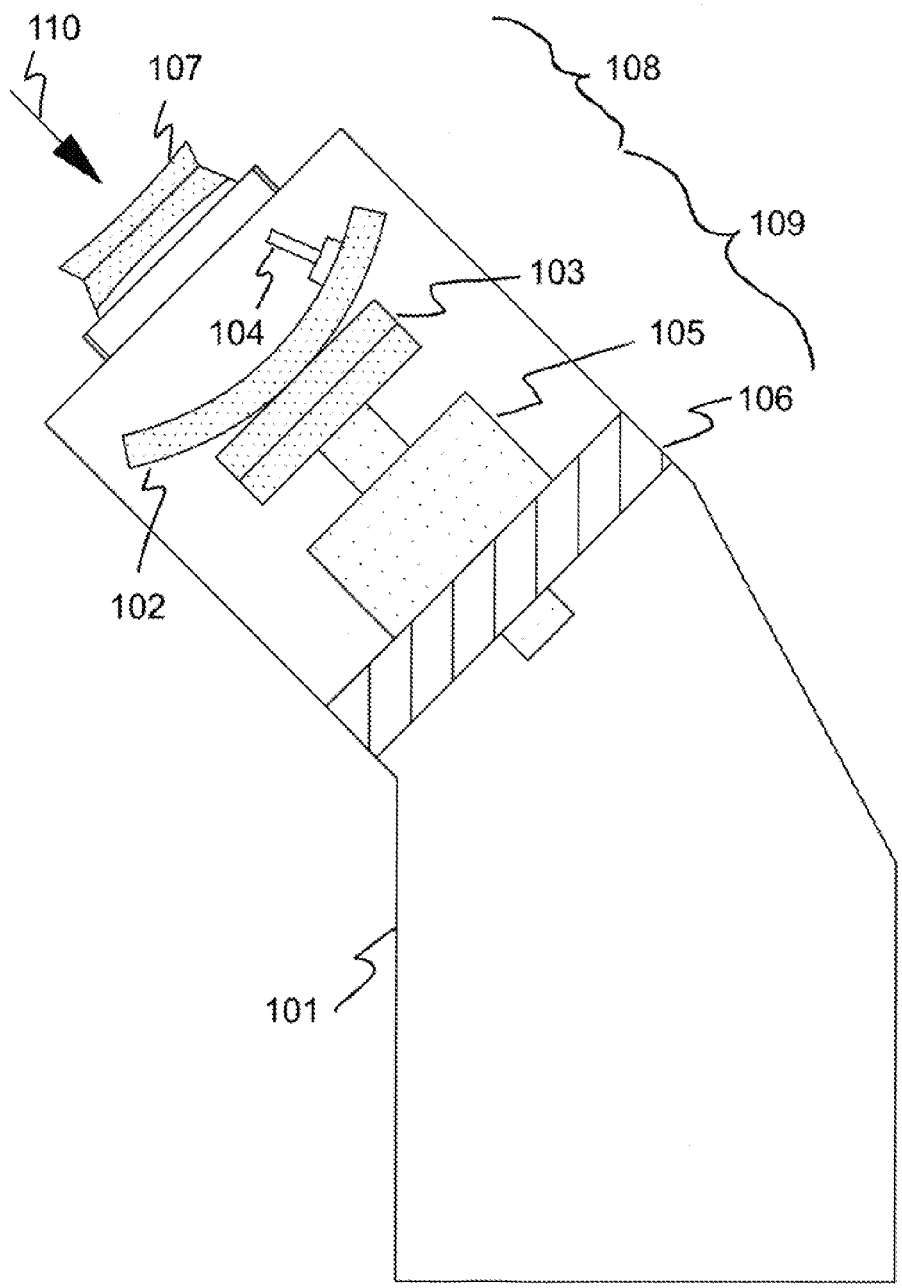
FIG. 1 is a schematic of the principal elements of a prior art ultrasound eye scanning device.

FIG. 1 is a schematic of the principal elements of a prior art ultrasound eye scanning device such as described in U.S. Pat. No. 8,317,709, entitled "Alignment and Imaging of an Eye with an Ultrasonic Scanner." The scanning device 101 of this example is comprised of a disposable eyepiece 107, a scan head assembly 108 and a positioning mechanism 109. The scan head assembly 108 is comprised of an arcuate guide 102 with a scanning transducer 104 on a transducer carriage which moves back and forth along the arcuate guide track 102, and a linear guide track 103 which moves the arcuate guide track 102 back and forth (as described in FIG. 3). The positioning mechanism 109 is comprised of an x-y-z and beta mechanisms 105 (described in FIG. 4) mounted on a base 106. The base 106 is rigidly attached to the scanning device 101. A longitudinal axis 110 passes generally through a center of the head assembly 108 and is substantially perpendicular to a face of the eyepiece 107. A video camera (not shown) may be positioned within the scanning device 101 and aligned with the longitudinal axis 110 to provide an image of a patient's eye through the eyepiece 107. The scanning device 101 is typically connected to a computer (not shown) which includes a processor module, a memory module, a keyboard, a mouse or other pointing device, a printer, and a video monitor. One or more fixation lights (not shown) may be positioned within the scanning device at one or more locations. The eyepiece 107 may be disposable as described in FIG. 5.

The positioner assembly 109 and scan head assembly 108 are both fully immersed in water (typically distilled water) which fills the chamber from base plate 106 to the top of the chamber on which the eyepiece 107 is attached.

A patient is seated at the scanning device 101 with one eye engaged with the disposable eyepiece 107. The patient is typically directed to look downward at one of the fixation lights during a scan sequence. The patient is fixed with respect to the scanning device 101 by a headrest system such as shown, for example, in FIG. 4, and by the eyepiece 107.

An operator using a mouse and/or a keyboard and the video monitor, for example, inputs information into the computer selecting the type of scan and scan sequences as well as the desired type of output analyses. The operator using the mouse and/or the keyboard, the video camera located in the scanning machine, and the video screen, centers a reference marker such as, for example, a set of cross hairs displayed on the video screen on the desired component of the patient's eye which is also displayed on video screen. This is done by setting one of the cross hairs as the prime meridian for scanning. These steps are carried out using the positioning mechanism which can move the scan head in the x, y, z and beta space (three translational motions plus rotation about the z-axis). The z-axis is parallel to the longitudinal axis 110. Once this is accomplished, the operator instructs the computer to proceed with the scanning sequence. Now the computer processor takes over the procedure and issues instructions to the scan head 108 and the scanning transducer 104 and receives positional and imaging data. The computer processor proceeds with a sequence of operations such as, for example: (1) with the transducer carriage substantially centered on the arcuate guide track, rough focusing of the scanning transducer 104 on a selected eye component; (2) accurately centering of the arcuate guide track with respect to the selected eye component; (3) accurately focusing the scanning transducer 104 on the selected feature of the selected eye component; (4) rotating the scan head assembly 108 through a substantial angle (including orthogonal) and repeating steps (1) through (3) on a second meridian; (5) rotating the scan head back to the prime meridian; (6) initiating a set of A-scans along each of the of selected scan meridians, storing this information in the memory module; (7) utilizing the processor, converting the A-scans for each meridian into a set of B-scans and then processing the B-scans to form an image associated with each meridian; (8) performing the selected analyses on the A-scans, B-scans and images associated with each or all of the meridians scanned; and (9) outputting the data in a preselected format to an output device such as a printer. As can be appreciated, the patient's head must remain fixed with respect to the scanning device 101 during the above operations when scanning is being carried out, which in a modern ultrasound scanning machine, can take several tens of seconds.

An eyepiece serves to complete a continuous acoustic path for ultrasonic scanning, that path extending in water from the transducer to the surface of the patient's eye. The eyepiece 107 also separates the water in which the patient's eye is immersed (typically a saline solution) from the water in the chamber (typically distilled water) in which the transducer guide track assemblies are contained. The patient sits at the machine and looks down through the eyepiece 107 in the direction of the longitudinal axis 110. Finally, the eyepiece provides an additional steady rest for the patient and helps the patient's head to remain steady during a scan procedure.

Mechanisms for General Ultrasound Scanning

Figure 2:
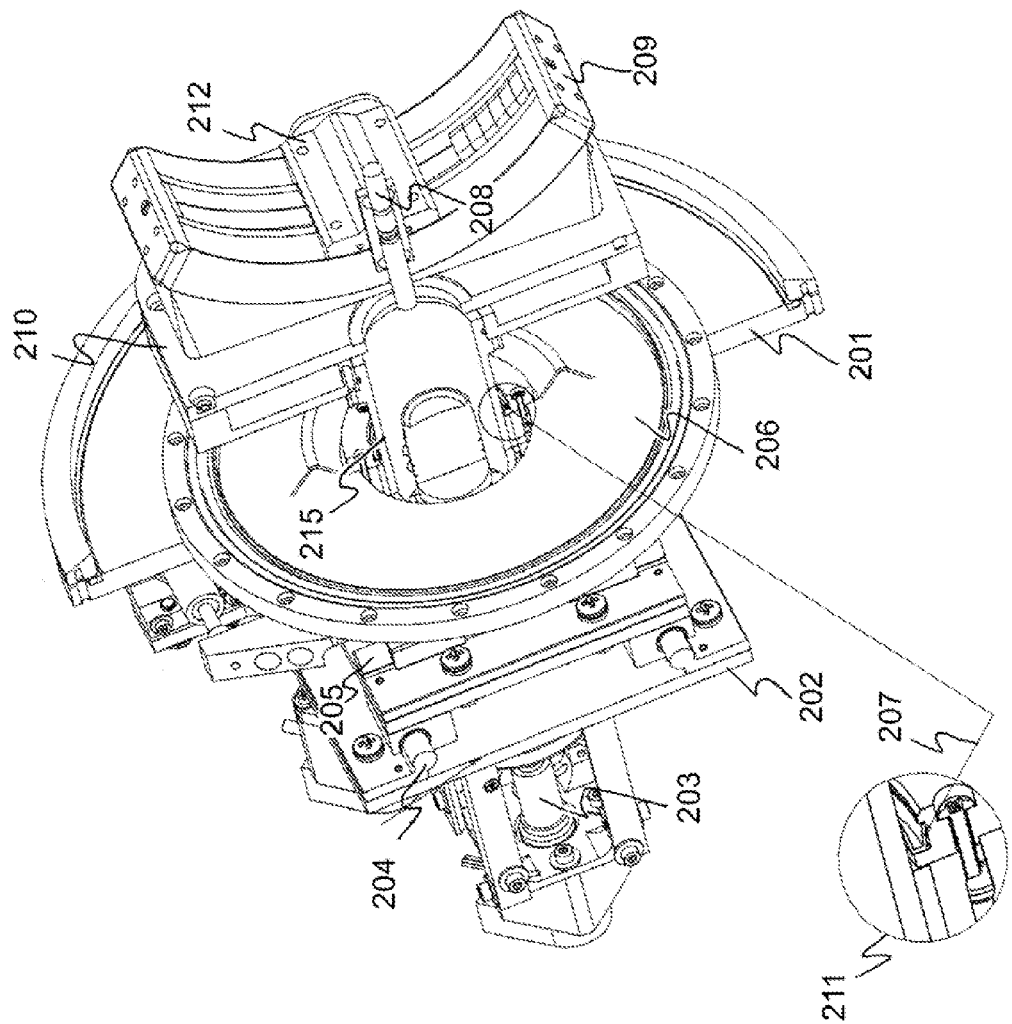
FIG. 2 illustrates a prior art arc scanning head positioning mechanism.
Figure 2:
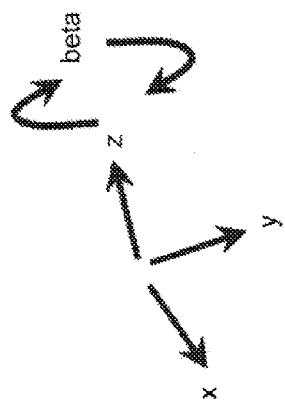

FIG. 2 illustrates a compact scan head positioning mechanism which has been disclosed previously in U.S. patent application Ser. No. 12/347,674, entitled "Innovative Components for an Ultrasonic Arc Scanning Apparatus." FIG. 2 shows a prior art scan head assembly comprised of scan head mount structure 210 and an arcuate guide track 209. The arcuate guide track 209 is comprised of an ultrasonic transducer 208 mounted on a transducer carriage 212. The transducer carriage 212 can be moved back and forth along arcuate guide track 209 to perform an arc scan. The scan head assembly is attached to a main positioner arm 215 (shown in a sectional view).

The scan head mount structure 210, arcuate guide track 209, transducer carriage 212, and ultrasonic transducer 208 are operative while immersed in water and are sealed from the rear portion of the positioning mechanism by a translational seal 206 and a combined z-axis and rotational seal 207. The translational seal 206 is typically formed by a large rubber membrane that can flex with the small x and y motions required by the scanning head positioner, although alternate sealing mechanisms may be employed. The combined z-axis seal and rotational seal 207 seal against the main positioner arm 215 which can both rotate and move in and out in the z-direction which lies substantially parallel to a longitudinal axis of an axial piston 203. Translational seal 206 is attached to a stationary plate 201 which, in turn, is affixed to the main arc scanner chamber (not shown) which, in turn, is fixed with respect to the patient being scanned. The combined z-axis and rotational seal 207, which is shown in close-up view 211, is typically formed by a circumferential groove type sealing mechanism with the groove facing into the water, although alternate sealing mechanisms may be employed. Available seals allow both rotation and axial translation of the main positioner arm 215 while maintaining a water tight seal. Plate 202 forms a platform for the x- and y-positioning mechanisms. Plate 202 is fixed relative to stationary plate 201. The scanning head assembly can be moved back and forth axially (the z-direction) by axial piston 203 or another suitable mechanism. The scanning head assembly can be rotated (the beta-direction) about the z-axis by a rotary stepping motor (not shown) or another suitable device. The scanning head assembly can be moved up and down (the y-direction) by piston 205 or another suitable mechanism. The scanning head assembly can be moved from side to side (the x-direction) by piston 204 or another suitable mechanism. The components to the left or rear of stationary plate 201 remain in ambient air while the components to the right or front of stationary plate 201 are immersed in water when the arc scanner is operational.

Typically, the scan head assembly is moved in the x-, y-, z- and beta directions to position the scan head assembly with respect to an eye component of interest. Although these motions are typically made rapidly under computer control, scans of the eye are typically not made during positioning. Once the scan head assembly is positioned with respect to the eye component of interest, scans are made by the transducer carriage 212 moving back and forth along the arcuate guide track 209. As described in U.S. patent application Ser. No. 12/347,674, the transducer carriage 212 moves along arcuate guide track 209 on a fluid bearing for smooth operation.

As described above, the scanning head assembly can be moved back and forth axially (the z-direction); rotated (the beta-direction) about the z-axis; moved up and down (the y-direction); and moved from side to side (the x-direction). It is therefore possible to move the entire scan head assembly in more complex motions by coordinating these movements to obtain scans that cannot be obtained by a simple arc scan. However, the mechanisms of the apparatus of FIG. 2, while suitable for rapid positioning movements, are not well-suited for rapid scanning motions necessary, for example, to obtain multiple images of an eye accommodating in real time. A more advanced device is illustrated in FIG. 3.

Figure 3:
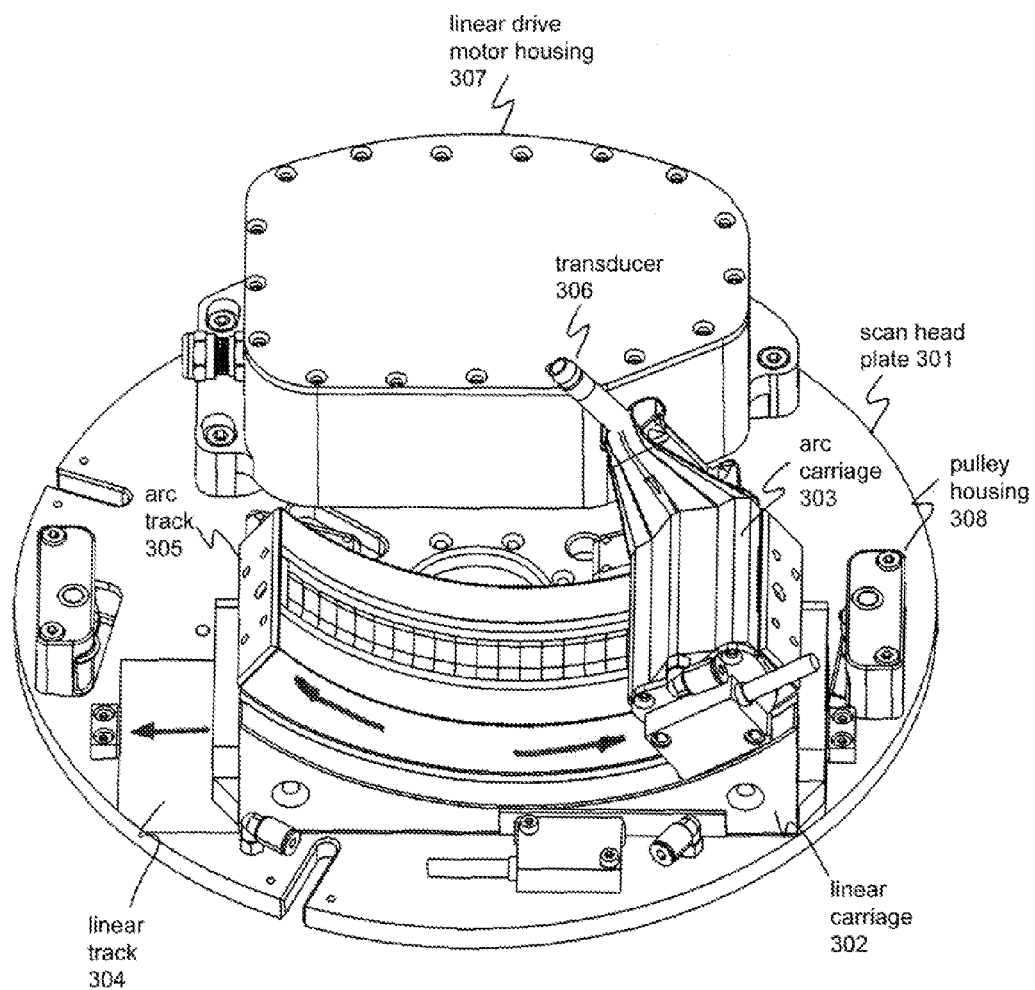
FIG. 3 illustrates a prior art scan head positioning mechanism and scan head capable of arcuate motion.

FIG. 3 illustrates a prior art scan head capable of linear motion, arcuate motion, and combined linear and arcuate motion. This scan head was disclosed previously in U.S. Pat. No. 8,317,709. A scan head plate 301 replaces scan head mount structure 210 of FIG. 2. Scan head plate 301 serves as the platform for a computer controlled linear carriage 302 and an arcuate carriage 303. Linear carriage 302 moves back and forth along a linear guide track 304. Arcuate carriage 303 moves back and forth along arcuate guide track 305. Typically, one of more transducers 306 or probes are mounted on the arcuate carriage 303. In this view, arc carriage 303 is at the rightmost limit of its travel along arcuate guide track 305 and linear carriage 302 is also at the rightmost limit of its travel on linear guide track 304. As can be appreciated, the motions of arcuate carriage 303 and linear carriage 302 can be controlled independently. For example, arcuate carriage 303 can move along arcuate guide track 305 or be parked anywhere along arcuate guide track 305 while linear carriage 302 moves along linear guide track 304. As another example, linear carriage 302 can be stationary while arcuate carriage 303 moves back and forth along arcuate guide track 305 to execute a pure arc scan. When arcuate carriage 303 is stationary and linear carriage 302 is moved, this is referred to as a linear scan. When both arcuate carriage 303 and linear carriage 302 are moved, this is referred to as combined scan. In this configuration, arcuate carriage 303 is moved along arcuate guide track 305 by an induction motor as described in U.S. patent application Ser. No. 12/347,674. Arcuate carriage 303 moves along arcuate guide track 305 on a fluid bearing which is also described in U.S. patent application Ser. No. 12/347,674. In the example of FIG. 3, an ultrasound scanning transducer 306 is mounted on the arcuate carriage 303. A longitudinal axis which passes generally through a center of the ultrasound scanning transducer 306 is aligned substantially parallel to a radius of curvature of arcuate guide track 305. Linear carriage 302 is moved along linear guide track 304 by a drive motor (not shown) housed in linear drive motor housing 307. This drive motor moves linear carriage 302 by a belt and pulley system (not shown except for typical pulley housing 308). Linear carriage 302 moves along linear guide track 304 on a fluid bearing similar to that used between arcuate carriage 303 and arcuate guide track 305. In operation, the scan head assembly of FIG. 3 is under water and is sealed from the x, y, z, beta positioner by a sealing means behind the scan head plate 301. Thus the entire scanning mechanism is positioned with respect to an eye for scanning by the x, y, z, beta positioner shown in FIG. 2, while the actual acoustic imaging scan motion is implemented by one or both of the linear and arcuate carriages 302 and 303. The scan head assembly of FIG. 3 allows rapid independent linear and arcuate motion combinations of the ultrasound scanning transducer such that various scan geometries can be implemented to image not only the cornea, iris and anterior lens surface, but also the posterior lens surface, the sulcus, the ciliary body, the suprachoroidal space and the zonules that attach the lens to the ciliary body.

The scan head assembly of FIG. 3 may also perform a controlled combined motion where the linear and arcuate motions are coordinated to produce a resultant pure arcuate motion of the arcuate probe carriage wherein the effective radius of curvature of the arcuate track is larger or smaller than the radius of curvature of the arcuate guide track. This combined motion is more completely described in U.S. Pat. No. 8,317,709.

Headrest

Figure 4:
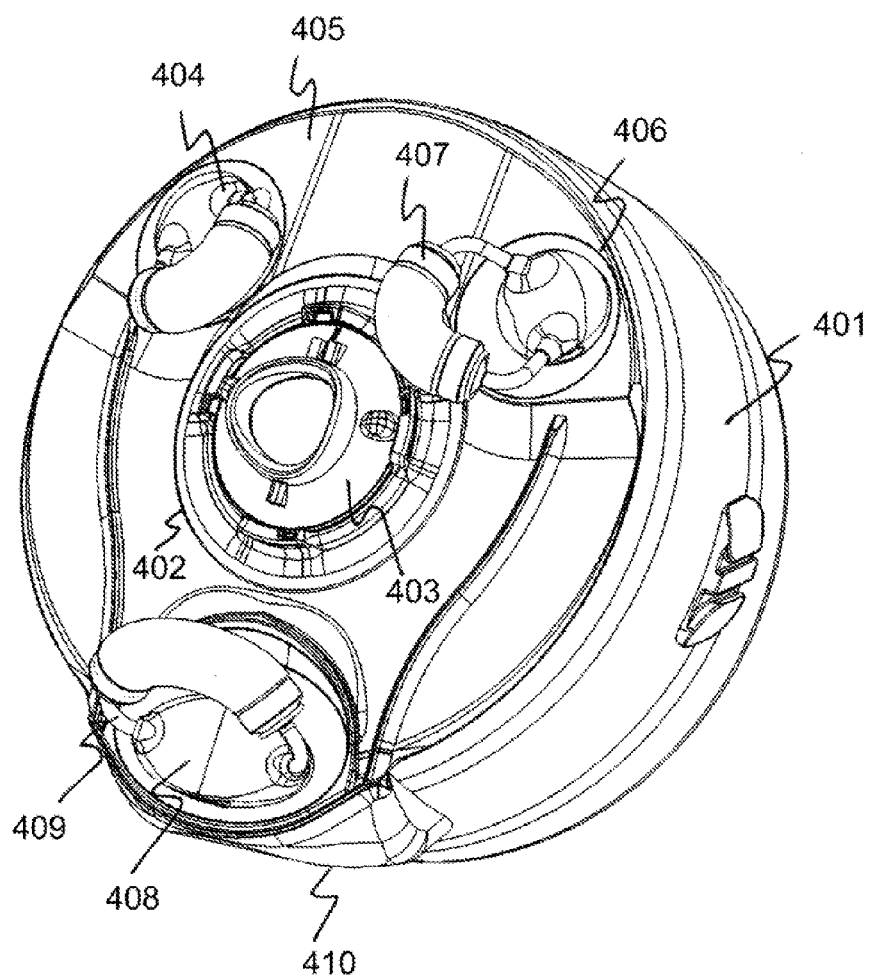
FIG. 4 is a schematic representation of a prior art a headrest for an eye scanning device.

FIG. 4 is a schematic representation of an example of a headrest system suitable for the present disclosure. FIG. 4 shows the body 405 of an ultrasonic imaging device 401. A disposable eyepiece 403 is shown attached to an eyepiece retaining ring 402 which is permanently attached to the body 405 of the ultrasonic imaging device 401. A headrest system is shown comprising a chin rest 408 and a two temple or forehead rests 404 and 406. The headrest system also includes an independently detachable water collector 410. The water collector 410 may be attached to the body 405 of the ultrasonic imaging device 401 in a variety of ways but preferably by magnetic attachment. Each of the chin rest 408 and two forehead rests 404 and 406 are comprised of a base plate such as 408, two connecting arms such as 409 and a central cushion such as 407.

An advantage of this headrest system is that each headrest subassembly 404, 406, and 408 is independently movable and the entire headrest system can be locked tight once the patient is in a comfortable position with respect to the scanner and with their eye properly positioned in the eyepiece. Another advantage of this headrest system is the headrest subassemblies have a relatively low profile and which allows the operator to see around the cushions to determine if the patient is properly positioned and to see the seal between the patient's face and the eyepiece to ensure the seal is good. Another advantage of this headrest system is that any one of the headrest subassemblies 404, 406, and 408 may be removed if the operator deems this necessary. This headrest system is fully described in U.S. patent application Ser. No. 12/754,444, entitled "Method of Positioning a Patient for Medical Procedures."

Eyepiece

An eyepiece serves to complete a continuous acoustic path for ultrasonic scanning, that path extending from the transducer to the surface of the patient's eye. The eyepiece also separates the water in which the patient's eye is immersed (typically a saline solution) from the water in the chamber (typically distilled water) in which the positioner and scan head assemblies are contained. Finally, the eyepiece provides a reference frame for the patient and helps the patient to remain steady during a scan.

Figure 5:
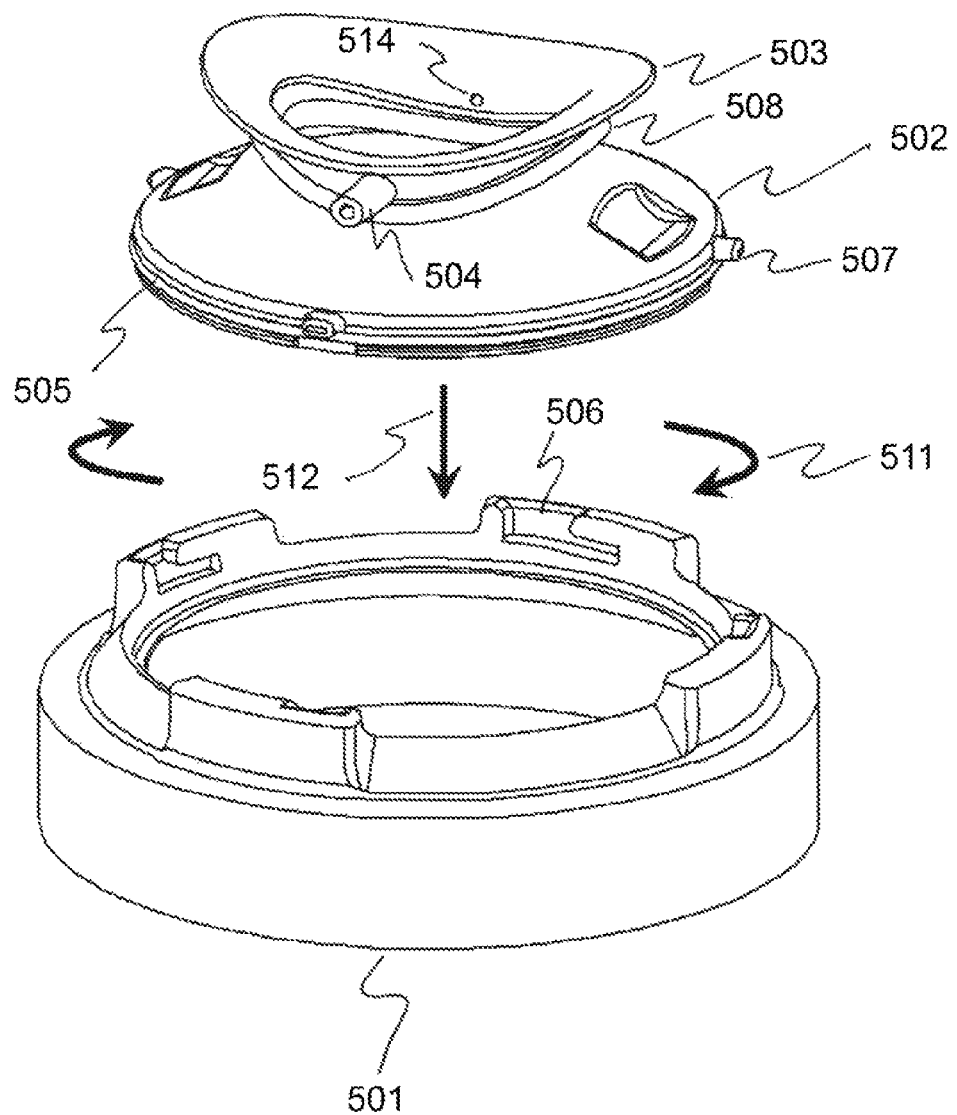
FIG. 5 illustrates a typical embodiment of a prior art eyepiece for an ultrasonic eye scanning device.

FIG. 5 illustrates an embodiment of an eyepiece that satisfies these requirements. The eyepiece consists of a mounting ring 501 and an eye seal ring 502. The mounting ring 501 is attached to and is typically a permanent part of the main scanner assembly. As shown here the mounting ring 501 has several attachment grooves 506 which can accept attaching mechanisms 507 on the eye seal ring 502. In this embodiment, the attaching mechanisms 507 are pushed down 512 into the attachment grooves 506 and then rotated 511 into position to form a mechanical connection that seals the eye seal ring 502 against the mounting ring 501 to prevent water leakage. This is also known as a bayonet type connection. There may be a sealing ring 505 which is compressed as the attaching mechanisms 507 are rotated 511 into position. The eye seal ring 502 has a soft rubber or foam contoured face seal 503 which is designed to seal against a typical human face around the eye that is to be scanned. The eye seal ring 502 is also shown with its water fill tube 504 on the top and a water drain tube 514 on the bottom. A sealed hygienic barrier (not shown) is formed as part of the eye seal ring 502 during manufacture and is typically located where the contoured face seal 503 is connected at location 508 to the main body of the eye seal ring 502.

The hygienic barrier or membrane may be permeable or semi-permeable to water as long as it is impermeable to bacteria, viruses, fungi, and other potentially harmful biological and chemical impurities. The membrane is preferably impermeable to water to provide superior isolation from biological and non-biological impurities that may be dissolved or carried in water. The membrane is preferably optically clear to allow a video camera to view the eye through the membrane. The membrane preferably passes acoustic and/or optical pulses without significant energy absorption. Eyepiece membranes have been made from several materials such as, for example, polyethylene, mylar, polypropylene, vinylidene chloride, and polyvinylidene chloride. A preferred material is medical grade polyethylene which has an acoustic impedance only somewhat higher than that of water (about 2.33 million $kg/m^2$-s compared to 1.54 million $kg/m^2$-s for water). The thickness of the membrane is preferably in the range of about 10 to about 30 microns.

As described previously, the eye seal ring typically includes a soft rubber or foam contoured face seal which is designed to seal against a typical human face around the eye that is to be scanned. The contoured face seal may also be made from a foam material impregnated with, for example, mineral oil, to provide a superior sealing action against a typical human face around the eye. An alternative face sealing mechanism can also be provided by a hollow soft rubber or soft plastic ring molded into the removable eye seal ring that can be filled with water after the patient has placed their face against the eyepiece. This eyepiece and other methods of attachment are more completely described U.S. patent application Ser. No. 12/347,674.

Precision Scanning Apparatus

Together, the headrest and the eyepiece act to comfortably fix the patient's head and eye relative to the eye scanning apparatus and so minimize any unintended head motion during positioning and scanning operations.

Figure 6:
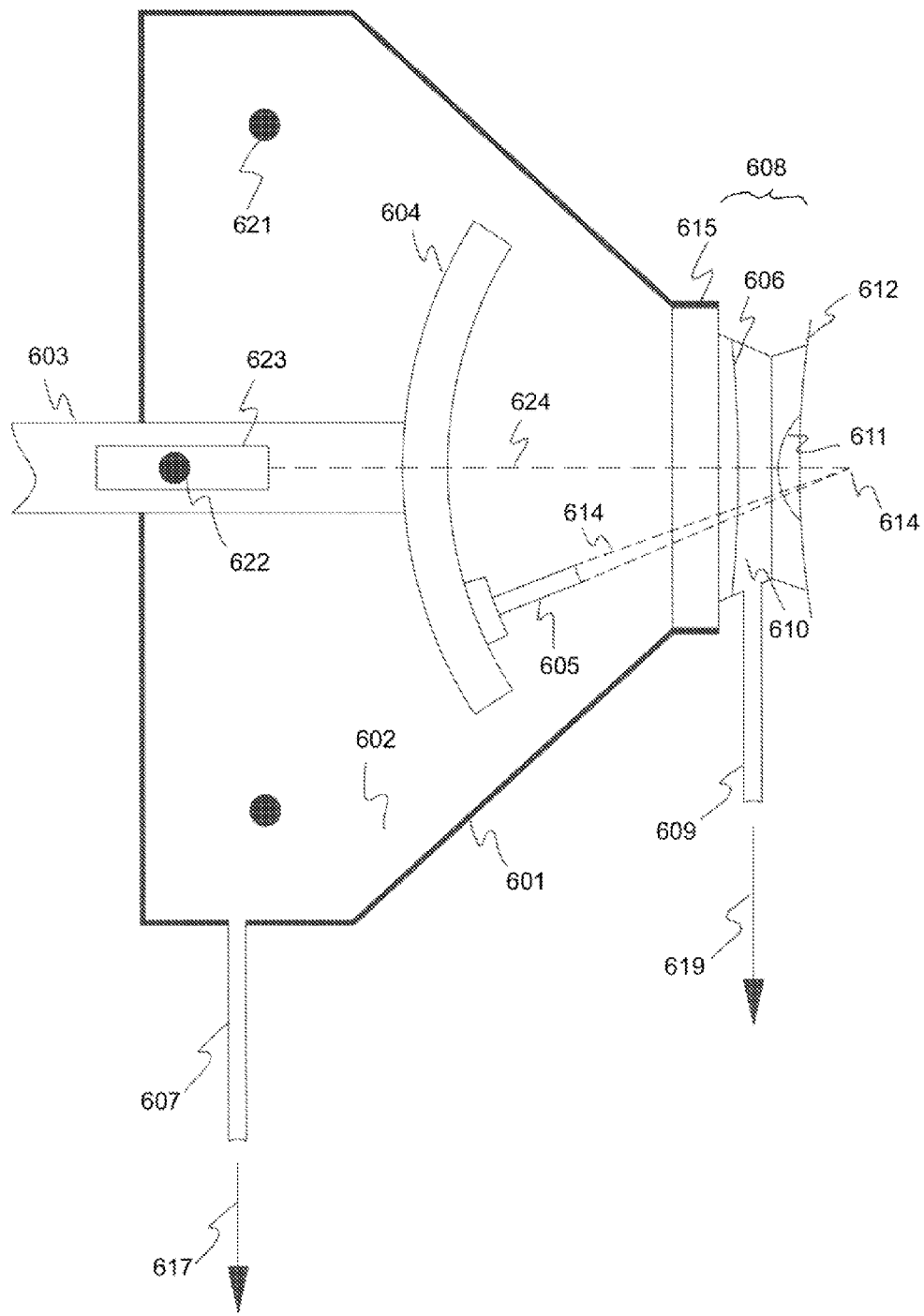
FIG. 6 is a schematic of an basic prior art arc scanning device.

FIG. 6 is a schematic illustration of a basic arc scanning device and shows the main elements of a prior art arc scanning device. This figure illustrates positioning of a transducer along an arc guide whose center of curvature is centered approximately on the center of curvature of an eye component of interest. FIG. 6 shows fixation lights 621 and 622 that allow the patient to fixate his or her eye to maintain it in a steady position during scanning FIG. 6 also shows an optical video camera 623 which may be used by the operator of the arc scanner to monitor the position of the patient's eye and to determine whether the patient's eye is open before a scan is initiated. When the patient fixes and eye on light 622, the visual axis of the eye 624 will align with the optical video camera 623.

The transducer and its arc guide assembly are positioned in a chamber 601 and are immersed in a medium suitable for conducting acoustic energy in the form of ultrasound such as water 602 to provide a transmission path for the acoustic signals. The patient's eye must also be immersed in water to provide continuity of the transmission path for the acoustic signal. This is accomplished by using a detachable eyepiece 608. FIG. 6 also shows a hygienic barrier 606 which separates the water chamber 601 in which the transducer 605 and arc scanning positioner, scan head and transducer carriage assembly 604 are immersed from the water 610 in which the patient's eye is immersed. This barrier 606 separates the water chamber 601 in which the transducer 605 and transducer carriage assembly 604 are contained from the water 610 in which the patient's eye is immersed. The arc guide assembly and associated components may be contaminated, for example, by particles from wearing mechanical components. The water 610 in which the patient's eye is immersed may be contaminated by bacteria or virus particles from the patient. As can be appreciated, the water 610 in which the patient's eye is immersed should be changed for every patient to prevent possible disease transmission. As can be further appreciated, the hygienic barrier 606 must be substantially transparent to ultrasound so as to maintain a clear acoustic transmission path between the patient's eye and the ultrasonic transducer 605. The hygienic barrier 606 is typically formed as part of a disposable eyepiece such as described in FIGS. 10 through 12 of U.S. patent application Ser. No. 12/347,674 and the accompanying text.

References are made herein to a medium suitable for conducting acoustic energy in the form of ultrasound. There are reasons to prefer that the medium be pure water or physiologic saline (also known as normal saline) but the embodiments do not exclude other media suitable for conducting acoustic energy in the form of ultrasound. Most other media present an increased danger to the patient's eye, even with a barrier interposed between the eye and the ultrasonic transducer. Barriers can leak or be breached, allowing the liquids on either side to mix, thus bringing a potentially harmful material into contact with a patient's eye.

It should be appreciated, however, that non-harmful, less-corrosive media and leak-proof, impenetrable barriers might be developed or discovered. This might allow different media other than pure water or physiologic saline to be used in this disclosure. Nothing about embodiments herein other than the hazards just described requires pure water or physiologic saline to be present in the chamber containing the transducer. All references herein to water should accordingly be understood as referring to any suitable liquid.

FIG. 6 further illustrates the continuity of an acoustic transmission path through water. A positioning arm 603 and transducer carriage assembly 604 on which the ultrasonic transducer 605 is mounted are positioned in the chamber 601 of water 602. An ultrasonically transparent hygienic barrier 606 separates chamber 601 from the interior of an eyepiece 608. The eyepiece 608 contains a separate volume of water 610 (typically a saline solution which is preferably sterilized) which fills the interior of the eyepiece 608 and contacts a patient's eye surface 611. The eyepiece 608 is connected and sealed to the main chamber 601 of the arc scanning device, and is also sealed against the patient's face 612. As can be seen, there is a continuous path through water from the transducer 605 to the patient's eye surface 611 for the efficient passage of acoustic energy 614. The hygienic barrier 606 readily passes acoustic energy without alteration, thus forming a portion of the continuous path between the transducer 605 and the patient's eye surface 611. Since the acoustic impedance of the patient's eye is approximately that of water, the acoustic energy from the transducer can be efficiently transmitted into the eye and reflected back from an eye component, such as for example, the surface of the cornea, to the transducer. Also shown in FIG. 6 are a water fill tube 607 for the main chamber 601 and a separate water fill tube 609 for the eyepiece 608. Fill tubes 607, 609 may be used to add or remove water from the chamber and eyepiece as indicated by arrows 617 and 619. As can be appreciated, the water used in the eyepiece can be distilled or slightly saline to match the salinity of the eye, and the water used in the eyepiece can be introduced at a temperature that is comfortable for the patient.

As can be appreciated, the fluid in the eyepiece 608, the hygienic membrane or barrier 606 and the water in the main chamber 601 are preferably optically transparent to allow the video camera 623 to image the patient's eye and to allow the fixation light sources 621, 622 to be seen by the patient being scanned.

The arc scanning device includes a control and signal processing system which is not illustrated in FIG. 6. The control and signal processing system is described in FIG. 9, below.

Present Disclosure

Figure 7:
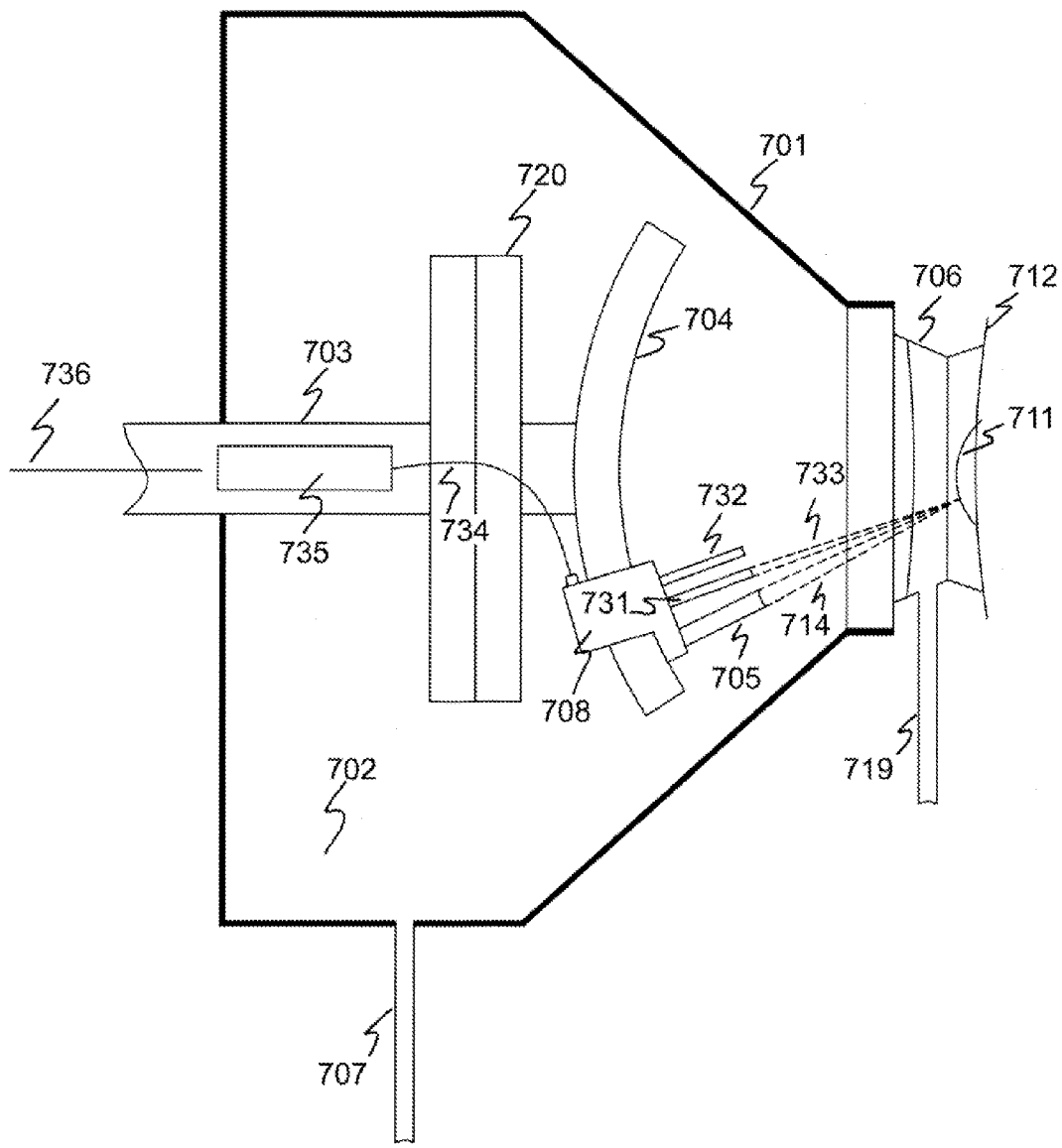
FIG. 7 illustrates the basic components of the apparatus of the present disclosure.

FIG. 7 illustrates an embodiment of a combined Very High Frequency Ultrasound ("VHFU") and Optical Coherence Tomography ("OCT") eye imaging system as part of a scan head. An OCT system is used herein as an example of an optical imaging system. The scan head is positioned with respect to a patient's eye using a positioner mechanism. The scan head may include a probe carriage for moving the VHFU and OCT probes. The positioner mechanism, the scan head, and probe carriage may be immersed in water. A disposable eyepiece may be connected to the system and filled separately with water to provide a continuous water transmission path from the probes to the surface of patient's eye. As discussed above, all references to water in all embodiments shall be understood to refer to any medium suitable for conducting acoustic and optical energy.

In another embodiment, a system with only an OCT probe is used with the positioner mechanism and a probe carriage to move the scan head and the OCT probe. In this configuration, the positioner mechanism, scan head, probe carriage and OCT probe may be immersed in water. A disposable eyepiece may also be connected to the system and filled separately with water to provide a continuous water transmission path from the probe to the surface of patient's eye.

In yet another embodiment, a system with only an OCT probe is used with the positioner mechanism. In this embodiment, the positioner mechanism and the scan head may not be immersed in water. In this embodiment, the disposable eyepiece may be replaced by an eyepiece apparatus that would only be used to position the patient's eye with respect to the imaging device.

The general components of an embodiment of a combined VHFU and OCT imaging system are shown in FIG. 7 with particular attention to the components in the scanning head which are unique to the combined imaging system. The components of the VHFU scanning system are disclosed and described in more detail in U.S. patent application Ser. No. 12/347,674.

A chamber 701 of water 702 is shown with a positioning arm 703, a linear guide track 720, and an arcuate guide assembly 704 on which a probe carriage 708 is mounted. The positioning arm 703 may rotate about a longitudinal axis 736 which passes generally through a center of the positioning arm 703 and which is substantially perpendicular a rear wall of the chamber 701. The positioning arm 703 may also move back and forth axially in the direction of the longitudinal axis 736. The linear guide track 720 is interconnected to the positioning arm 703 and substantially perpendicular to the longitudinal axis 736. The arcuate guide assembly 704 is interconnected to the linear guide track 720 and the sagitta of the arcuate guide assembly 704 is substantially perpendicular to the longitudinal axis 736. The arcuate guide assembly 704 may move back and forth on the linear guide track 720. The probe carriage 708 is mounted on the arcuate guide assembly 704 and may move in an arcuate motion along the arcuate guide assembly 704. The motions of the positioning arm 703, the linear guide track 720, and the arcuate guide assembly 704 can be controlled independently. Because of its connection to the positioning arm 703, the linear guide track 720, and the arcuate guide assembly 704, the probe carriage 708 may be rotated about the longitudinal axis 736, may be moved axially along the longitudinal axis 736, and may be moved in a combination of linear and arcuate motions along the linear guide track 720 and the arcuate guide assembly 704.

An ultrasonically and optically transparent barrier (not shown) separates chamber 701 from the interior of an eyepiece 706. The eyepiece 706 contains a separate volume of water which fills the interior of the eyepiece 706 and contacts a patient's eye surface 711. The eyepiece 706 is connected and sealed to the main chamber 701 of the scanning device, and is also sealed against the patient's face 712.

Also shown in FIG. 7 are a water fill tube 707 for the main chamber 701 and a separate water fill tube 719 for the eyepiece 706. As can be appreciated, the water used in the eyepiece can be distilled or slightly saline to match the salinity of the eye, and the water used in the eyepiece can be introduced at a temperature that is comfortable for the patient.

Probe carriage 708 comprises an ultrasound transducer probe 705, an OCT probe 731 and an OCT reference arm 732. The ultrasound transducer probe 705 and OCT probe 731 are preferably focused at the same point on or within the patient's eye. Alternately, the probes 705, 731 can be substantially parallel and then offset by a small linear dimension. The ultrasound transducer probe 705 may be connected via an ultrasound cable (not shown) to the ultrasound recording apparatus (not shown). The OCT probe 731 and OCT reference arm 732 may be connected via optical fibers 734 to the OCT recording apparatus 735. The combined VHFU and OCT imaging system may include one or more position tracking sensors (not shown). The one or more of the position tracking sensors may be fixed relative to the positioning arm 703. The position tracking sensors can continuously monitor the patient's eye or any other anatomical feature for movement during a scan to remove unwanted movement of the feature from the scan.

FIG. 7 illustrates continuous acoustic 714 and optical 733 transmission paths for the efficient passage of acoustic and optical energy. The continuous paths proceed from the probes 705 and 731 through water to the patient's eye surface 711. The barrier separating the chamber 701 and eyepiece 706 readily passes acoustic and optical energy with minimal alteration, thus forming a portion of the continuous paths between the probes 705 and 731 and the patient's eye surface 711. Since the acoustic and optical impedances of the patient's eye is approximately those of water, the energy from the probes can be efficiently transmitted into the eye and reflected back from an eye component, such as for example, the surface of the cornea, to the probe.

A key element of this disclosure is the inclusion of an OCT imaging apparatus to the probe carriage which heretofore only included an ultrasound probe. In the embodiment illustrated in FIG. 7, the OCT reference arm 732, the OCT probe 731, 2×2 fiber optic coupler (described in conjunction with FIG. 8) and collimators (for the reference and sample arms) are added to the probe carriage 708 of the arcuate guide assembly 704 which is in turn immersed in water. This carriage 708 is part of the arcuate motor that moves about the cornea surface such that the probes in the carriage are substantially perpendicular to the cornea surface throughout a scan. The probes 705, 731 are then able to conduct scans in an arcuate path across the entire cornea surface. The OCT probe 731 is co-mounted with the ultrasound transducer probe 705 with a small angular offset to the ultrasound transducer probe 705 to maintain both the OCT probe 731 and the ultrasound transducer probe 705 aligned substantially perpendicular relative to the cornea surface. To minimize potential "glare" effects from high reflectance at exact perpendicularity common to many OCT systems, the OCT probe 731 could be aimed at an angle slightly oblique relative to the cornea surface. Because the optical beam is transmitted through water and the refraction coefficient difference between water and the cornea layers is small, any refraction correction which may be required will be small if the optical path 733 of the beam of the OCT probe 731 is slightly oblique relative to the cornea surface.

The OCT reference arm 732 is illustrated in FIG. 7 mounted next to the OCT probe 731 on the probe carriage 708 but could be mounted at any location on the probe carriage 708 that would be advantageous to efficient operation of the OCT reference arm 732 and to design requirements of the probe carriage 708.

As can be appreciated, a positioning arm 703 and a probe carriage 708 on an arcuate guide assembly 704 can be used for an embodiment of a system comprised of an OCT probe 731 and an OCT reference arm 732 with no ultrasound transducer probe 705. In this embodiment, the OCT probe 731 may move in an arcuate path that keeps the OCT probe 731 substantially perpendicular to the surface of the cornea or lens. Keeping the OCT probe 731 aligned substantially perpendicular to the surface of the cornea or lens minimizes refraction errors in the OCT beam. In this embodiment, the chamber 701 and eyepiece 706 may be filled with air instead of water. However, if water is used in the chamber 701 and eyepiece 706, then the refraction errors in the OCT beam are further minimized as the OCT beam passes from water into the eye with a significantly smaller change in index of refraction.

The combined VHFU and OCT eye imaging system includes a control and signal processing system. The control and signal processing system is further described in conjunction with FIG. 9, below.

Figure 8:
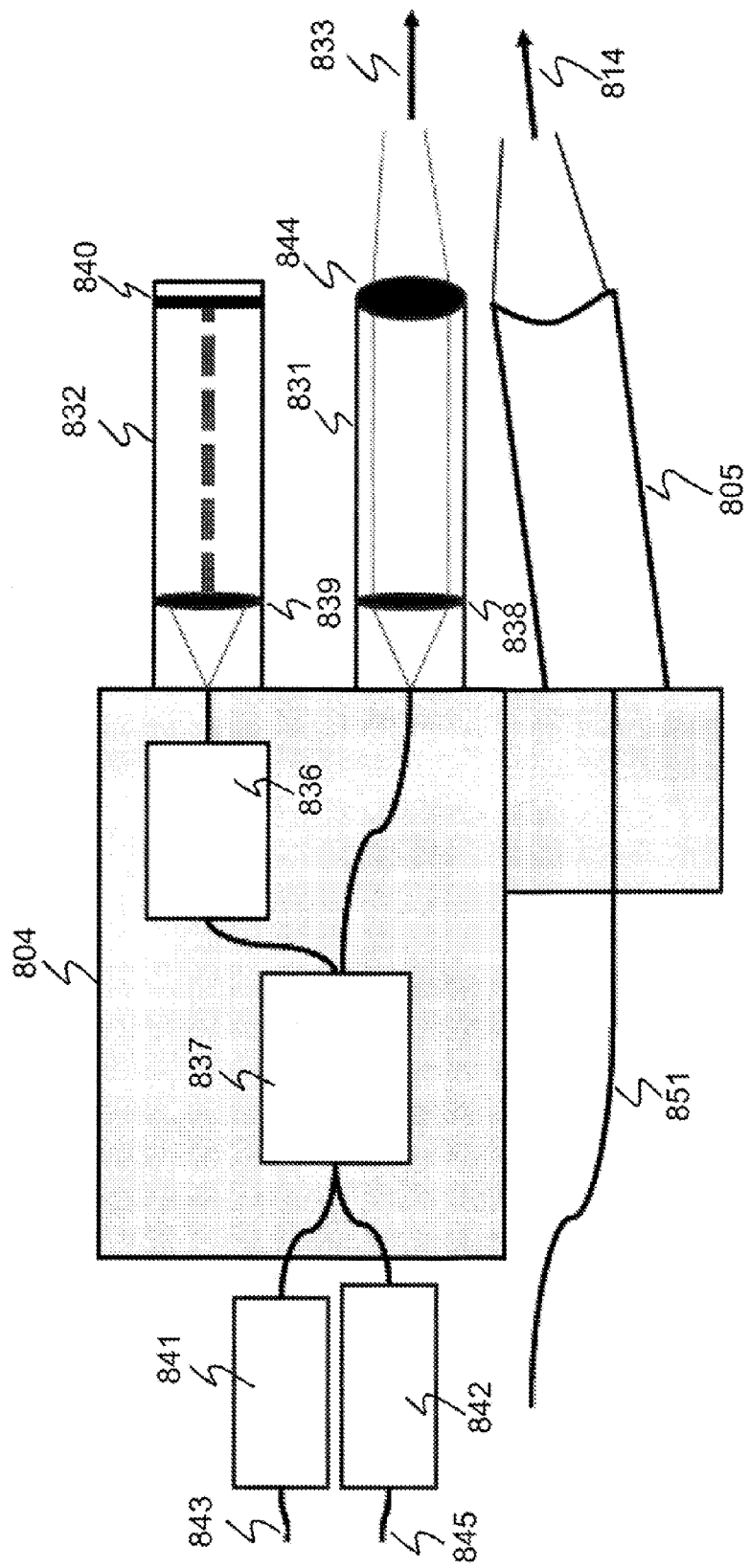
FIG. 8 illustrates the basic components of a combined optical and ultrasound imaging device on a probe carriage.

FIG. 8 illustrates the basic components of an embodiment of a combined optical and ultrasound system mounted on a probe carriage. FIG. 8 shows a probe carriage 804 on which are mounted an ultrasound transducer probe 805, an OCT probe 831 and an OCT reference arm 832. The OCT reference arm 832 may be comprised of a fixed mirror 840 and a collimator 839. The OCT probe 831 is commonly comprised of a collimator 838 and a focusing lens 844. For example, focusing lens 844 can be used for cornea scanning where the OCT probe may be focused on the cornea surface. The diopter of lens 844 would depend on whether the optical pulse path is through air or water. For imaging other eye components, a different focusing lens 844 may be required.

The OCT reference arm 832 is connected to an optical delay line 836. The OCT probe 831 and optical delay line 836 are connected to a 2×2 fiber optic coupler 837 which is in turn connected to a broad band light source 841 and a spectrometer 842. Cable 843 is a power cable that connects broad band light source 841 to a power source. Cable 845 is a data and power cable which powers spectrometer 842 and also sends the spectrometer data back to the control device. During scanning, the ultrasound transducer probe 805 emits and receives an ultrasound pulse 814 and the OCT sample arm probe emits and receives an optical pulse 833.

One important benefit of this embodiment is that the OCT reference arm 832 and OCT probe 831 are co-mounted on the carriage 804. By co-mounting the OCT probe 831 and the OCT reference arm 832 on the probe carriage 804, the optical fibers connected to the probe 831 and the arm 832 move or bend equally relative to one another during scanning as the probe carriage 804 moves. Preventing the optical fibers from bending unequally eliminates a common mode source of noise from optical fiber/cable flexing because bending and/or flexing of optical fibers and cables causes time delays. To prevent this source of noise, the 2×2 fiber optic coupler 837 and collimators are also mounted on the probe carriage 804 along with the OCT probe 831 and OCT reference arm 832. Careful treatment of any optical fibers from the broad band light source 841 and spectrometer 842 may also be required to minimize any noise from fiber flexing during the scan.

The optical delay line 836 may be used in the OCT reference arm 832 to compensate for the optical path difference between the fixed mirror 840 in the reference arm 832 and the distance to the sample as would be expected by the standoff from the distal end of the OCT probe 831 to the cornea surface. This distance could be as much as about 10 to about 20 mm.

Unlike prior art OCT systems, in the present disclosure the optical means is not scanned across the image field because the reference and sample arms themselves are scanned across the image field. This eliminates one or more fast acting mirrors typically required by prior art OCT imaging systems and also allows for significant reduction in the diameter of the collimating and focus lenses because the beam will be fixed on the central axis of the optics only. This reduction in OCT optical system size is important because system design requirements for rapid actuation of the arcuate motor requires the design to minimize weight and volume of anything mounted on the probe carriage.

Another embodiment of the current disclosure replaces the dual path created by the reference arm and the OCT probe of the OCT interferometer with a common mode interferometer. In this embodiment, a partially reflective element is placed between the final OCT probe lens at its distal end. The OCT probe then performs the functions of both the OCT probe and the reference arm within the same element. This would eliminate the physical reference arm, eliminate a potential source of noise, reduce complexity, and further lighten the probe carriage.

Control and Signal Processing

Figure 9:
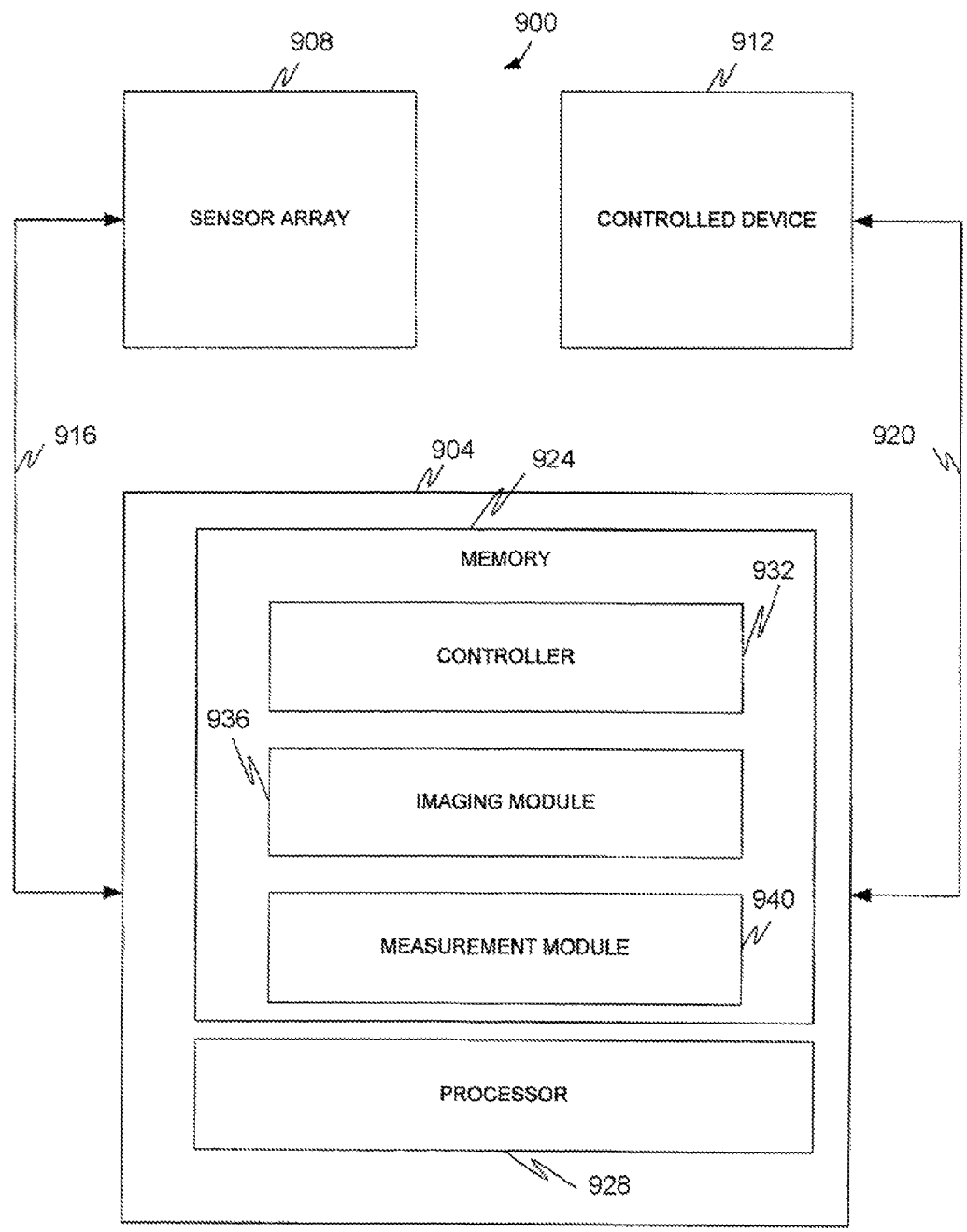
FIG. 9 is a block diagram of a control architecture for a combined optical and ultrasound system.

FIG. 9 depicts a control and signal processing system for any of the embodiments of the present disclosure discussed above. The system 900 includes a sensor array 908 and a controlled device 912 in signal communication via, duplexed channels 916 and 920, with a computer 904.

The sensor array 908 comprises linear or angular position sensors that, among other things, track the relative and/or absolute positions of the various movable components and the alignment of various stationary and moveable components, such as, but not limited to, the one or more position tracking sensors, the positioning arms 603 and 703 and probe carriage assembly 604, the fixation lights 621, 622, the optical video camera 623, the arcuate guide assembly 704, the ultrasound transducer probes 605, 705 and 805, the probe carriage 708, the linear guide track 720, the OCT probes 731, 831, the OCT reference arms 732, 832, the OCT recording apparatus 735, the probe carriage 804, the optical delay line 836, the collimators 838 and 839, the fixed mirror, the broad band light source 841, the spectrometer 842, the motors to move the position arms, motors to move the arcuate guide assembly, and motors to move the probe carriage. The sensor array may comprise any suitable type of positional sensors, including inductive non-contact position sensors, string potentiometers, linear variable differential transformers, potentiometers, capacitive transducers, eddy-current sensors, Hall effect sensors, proximity sensors (optical), grating sensors, optical encoders (rotary or linear), and photodiode arrays. Candidate sensor types are discussed in U.S. patent application Ser. No. 12/347,674.

The controlled device 912 is any device having an operation or feature controlled by the computer 904. Controlled devices include the various movable or activatable components, such as, but not limited to, the one or more position tracking sensors, the positioning arms 603 and 703, the transducer carriage assembly 604, the fixation lights 621, 622, the optical video camera 623, the arcuate guide assembly 704, the ultrasound transducer probes 605, 705 and 805, the probe carriage 708, the linear guide track 720, the OCT probes 731, 831, the OCT reference arms 732, 832, the OCT recording apparatus 735, the probe carriage 804, the optical delay line 836, the collimators 838 and 839, the fixed mirror, the broad band light source 841, the spectrometer 842, the motors to move the position arms, motors to move the arcuate guide assembly, and motors to move the probe carriage.

The computer 904 may comprise a software-controlled device that includes, in memory 924, a number of modules executable by a processor 928. The executable modules include a controller 932 to receive and process positioning signals from the sensor array 908 and generate and transmit appropriate commands to the monitored controlled device 912, an imaging module 936 to receive and process A- and B-scan images to produce two-, three-, or four-dimensional images of selected ocular components or features, and a measurement module 940 to determine, as discussed above, the dimensions and/or volumes of selected ocular components and/or features. The imaging algorithm used by the imaging module 936 is further discussed in U.S. patent application Ser. No. 12/418,392.

In one embodiment, the controller 932 determines an adjustment to the position of the transducer and/or the OCT sample arm probe and the OCT reference arm based on receiving a control measurement input from the sensor array 908. In another embodiment, the controller 932 provides a control input to the drive mechanism of the probe carriage, the positioning arm, the arcuate guide assembly, and/or the linear guide track. In yet another embodiment, the controller 932 provides a control input to comprise controlling the power, frequency, signal/noise ratio, pulse rate, gain schedule, saturation thresholds, and sensitivity of the optical and/or ultrasound transducers. In still another embodiment, the controller 932 utilizes control algorithms comprising at least one of on/off control, proportional control, differential control, integral control, state estimation, adaptive control and stochastic signal processing. Controller 932 may also monitor and determine if any faults or diagnostic flags have been identified in one or more elements, such as the optical and/or ultrasound transducers and/or carriage.

In yet another embodiment, the disclosed systems and methods may be partially implemented in software that can be stored on a storage medium to include a computer-readable medium, executed on a programmed general-purpose computer with the cooperation of a controller and memory, a special purpose computer, a microprocessor, or the like. In these instances, the systems and methods of this disclosure can be implemented as a program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

In one embodiment, one or more computers are used to control, among other things, the combined VHFU and OCT imaging system, the scan head assembly, the OCT sample arm probe, OCT reference arm, and/or the ultrasound transducer and/or the position sensor(s). In one embodiment, the user interacts with the computer through any means known to those skilled in the art, to include a keyboard and/or display to include a touch-screen display. The term "computer-readable medium" as used herein refers to any tangible storage and/or transmission medium that participates in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

The disclosure has been described with reference to the preferred embodiments. Modifications and alterations will occur to others upon a reading and understanding of the preceding detailed description. It is intended that the disclosure be construed as including all such modifications and alterations insofar as they come within the scope of the appended claims or the equivalents thereof.

A number of variations and modifications of the disclosures can be used. As will be appreciated, it would be possible to provide for some features of the disclosures without providing others.

The present disclosure, in various embodiments, includes components, methods, processes, systems and/or apparatus substantially as depicted and described herein, including various embodiments, sub-combinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, for example for improving performance, achieving ease and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the description of the disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. A scanning device, comprising:
    an instrument body that positions an eye of a patient, the instrument body comprising a chamber filled with a first fluid medium;
    a positioning assembly connected to the instrument body;
    a scan head connected to the positioning assembly, the scan head comprising an arcuate guide track and a probe carriage mounted on the arcuate guide track, wherein the arcuate guide track and the probe carriage are disposed in the first fluid medium of the chamber;
    the probe carriage having an optical coherence tomography (OCT) sample arm that emits an optical pulse, an OCT reference arm that emits a reference optical pulse, and an ultrasound imaging probe that emits an ultrasound pulse;
    an optical transmission path defined by the emitted optical pulse, wherein the optical transmission path forms a first angle with a longitudinal axis of the positioning assembly;
    an acoustic transmission path defined by the emitted ultrasound pulse, wherein the acoustic transmission path forms a second angle with the longitudinal axis of the positioning assembly, wherein the first angle is distinct from the second angle;

an eyepiece having an interior surface defining a partially enclosed volume filled with a second fluid medium; and a fluid barrier positioned between the chamber of the instrument body filled with the first fluid medium and the partially enclosed volume of the eyepiece filled with the second fluid medium, wherein the fluid barrier is acoustically transparent and optically transparent.

2. The scanning device of claim 1, wherein the optical transmission path and the acoustic transmission path intersect at a point in the eye of the patient and the eye of the patient contacts the second fluid medium.

3. The scanning device of claim 1, further comprising one or more fixation lights positioned within the interior of the chamber to orient the eye of the patient.

4. The scanning device of claim 1, further comprising:

a linear guide track connected to the scan head, wherein the linear guide track linearly displaces the arcuate guide track along a length of the linear guide track.

* * * * *